(12) United States Patent
Yoshikawa et al.

(10) Patent No.: US 7,924,418 B2
(45) Date of Patent: Apr. 12, 2011

(54) INSPECTION APPARATUS AND METHOD

(75) Inventors: Hiroshi Yoshikawa, Kawasaki (JP); Kenji Saitoh, Atsugi (JP)

(73) Assignee: Canon Kabushiki Kaisha, Tokyo (JP)

( * ) Notice: Subject to any disclaimer, the term of this patent is extended or adjusted under 35 U.S.C. 154(b) by 447 days.

(21) Appl. No.: 12/171,642

(22) Filed: Jul. 11, 2008

(65) Prior Publication Data

US 2009/0015823 A1    Jan. 15, 2009

(30) Foreign Application Priority Data

Jul. 12, 2007 (JP) ................................. 2007-182954

(51) Int. Cl.
*G01N 21/00* (2006.01)

(52) U.S. Cl. .................................. 356/237.2; 356/237.3

(58) Field of Classification Search ........................ None
See application file for complete search history.

(56) References Cited

FOREIGN PATENT DOCUMENTS

JP        06-222013 A    8/1994

*Primary Examiner* — Gregory J Toatley
*Assistant Examiner* — Amanda H Merlino
(74) *Attorney, Agent, or Firm* — Canon USA Inc IP Division

(57) ABSTRACT

An inspection apparatus includes a captured image acquiring unit configured to acquire a captured image that is acquired by shooting an inspection target, an acquiring unit configured to acquire from the captured image a first image region and a second image region whose intensity distributions of reflected light with respect to an incident angle of illumination light emitted to the inspection target are different, and an image processing unit configured to perform image processing for performing different surface inspections on the first image region and the second image region respectively.

11 Claims, 18 Drawing Sheets

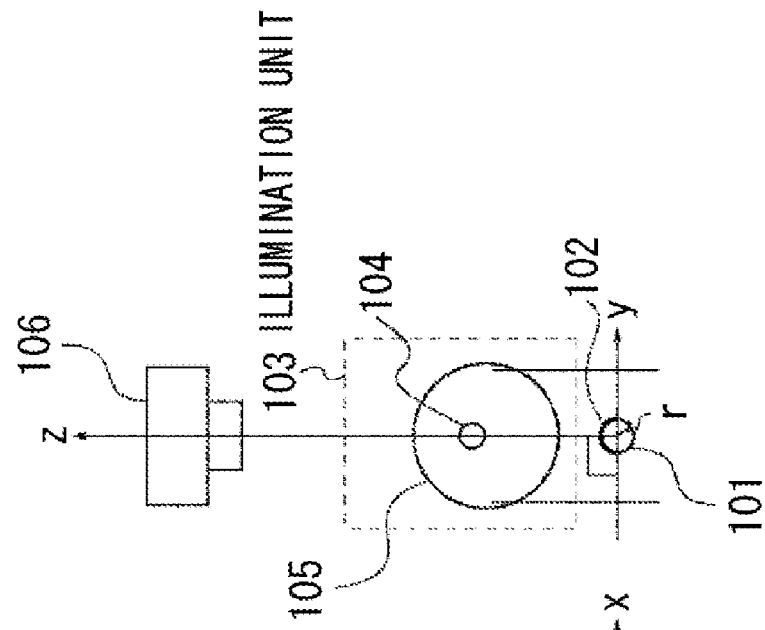
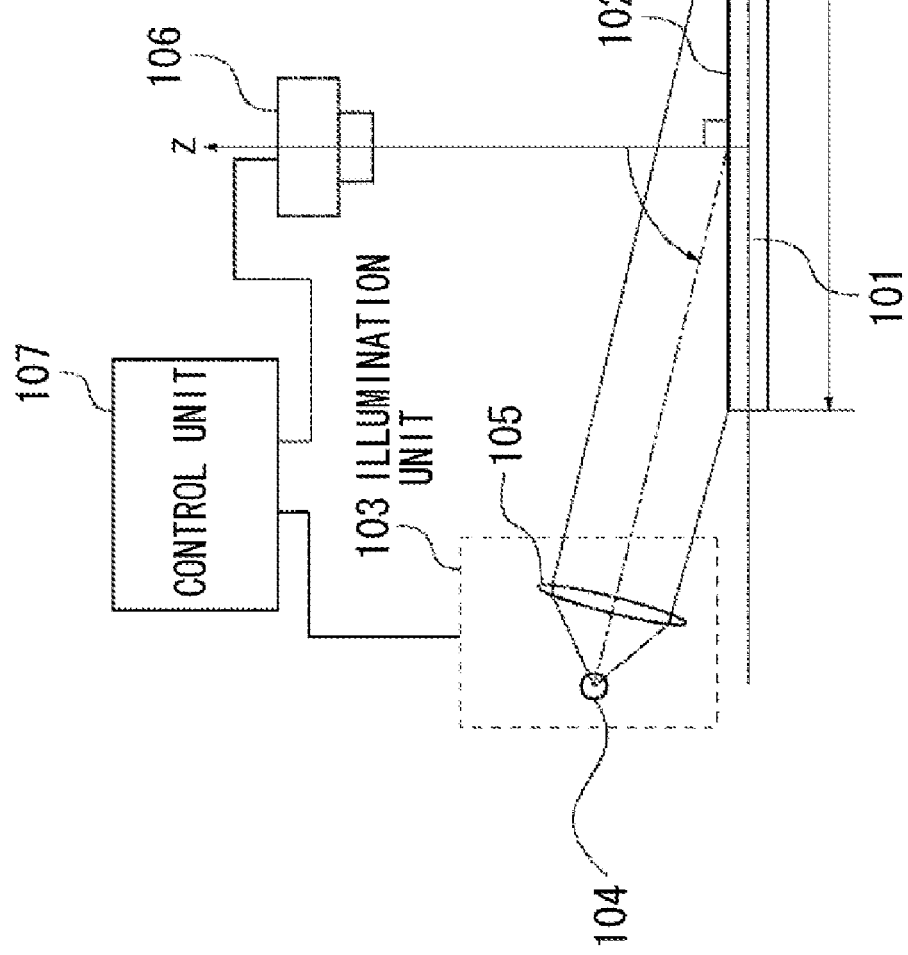
FIG. 1A
FIG. 1B

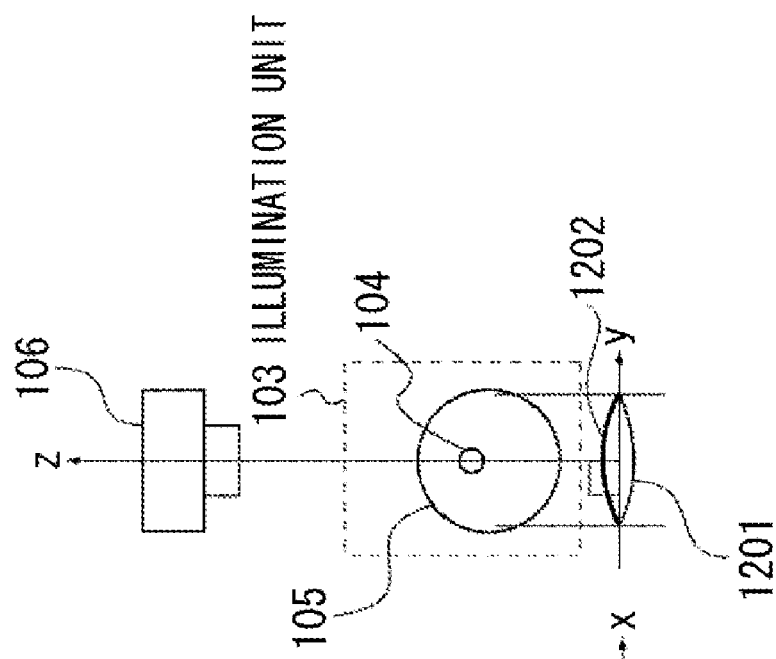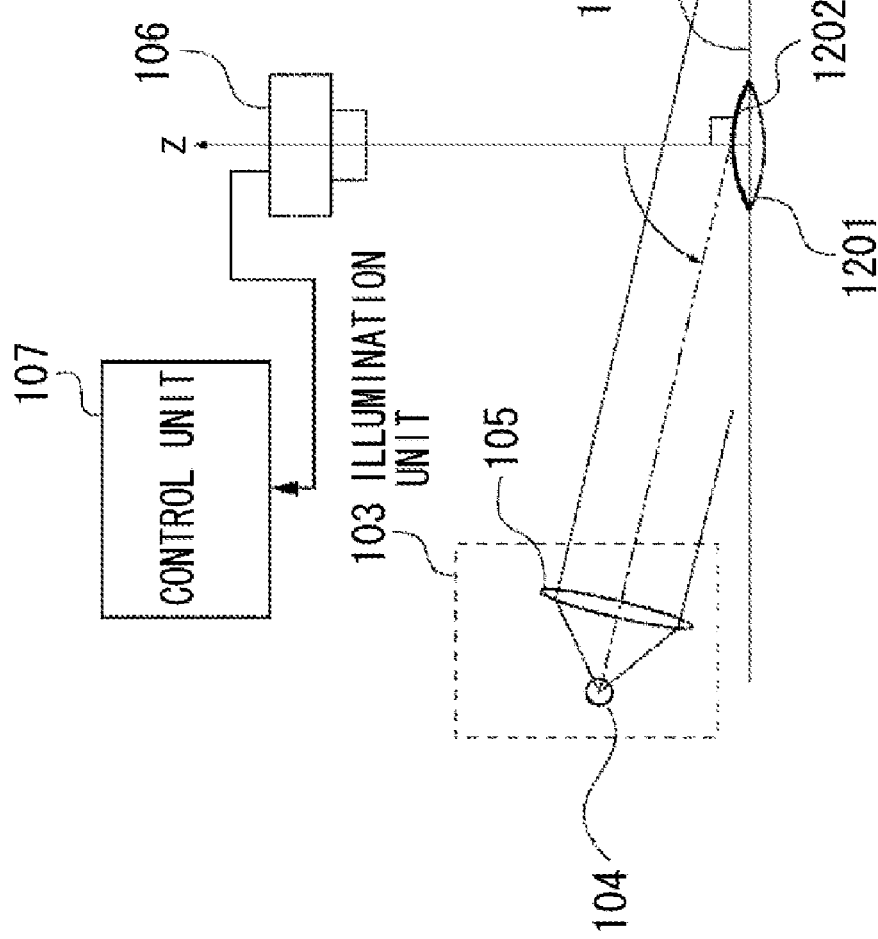

INSPECTION APPARATUS AND METHOD

BACKGROUND OF THE INVENTION

1. Field of the Invention

The present invention relates to an inspection apparatus that performs a process for performing surface inspection of an inspection target, and a method thereof.

2. Description of the Related Art

Conventionally, there is an inspection apparatus which detects a surface shape of an object to be inspected by irradiating a surface of the object with illumination light and detecting reflected light from the object.

In general, surface shapes of an object to be inspected differ according to manufacturing processes. In a case where a plurality of types of surface shape is to be detected, it is necessary to provide a plurality of inspection apparatuses that correspond to the surface shapes. Otherwise, a plurality of detection units needs to be included in one inspection apparatus.

Japanese Patent Application Laid-Open No. 06-222013 discusses an inspection apparatus including three types of illumination unit and two types of imaging unit. The inspection apparatus discussed in Japanese Patent Application Laid-Open No. 06-222013 detects three types of surface shape, i.e., scratch, stain, and bulge that appear on the surface of an object to be inspected, by switching operations between the three types of illumination unit and between the two types of imaging unit.

The inspection apparatus discussed in Japanese Patent Application Laid-Open No. 06-222013 changes image capturing conditions, acquires a plurality of images, and performs surface inspection to detect a plurality of types of surface shapes. Therefore, it is necessary to acquire a plurality of images under a plurality of imaging conditions according to a conventional technique, which makes the surface inspection process complex.

SUMMARY OF THE INVENTION

The present invention is directed to an inspection apparatus which can enables performing a plurality of types of surface inspection by capturing a single image.

According to an aspect of the present invention, an inspection apparatus includes a captured image acquiring unit configured to acquire a captured image that is acquired by shooting an inspection target, an acquiring unit configured to acquire from the captured image a first image region and a second image region whose intensity distributions of reflected light with respect to an incident angle of illumination light emitted to the inspection target are different, and an image processing unit configured to perform image processing for performing different surface inspections on the first image region and the second image region respectively.

Further features and aspects of the present invention will become apparent from the following detailed description of exemplary embodiments with reference to the attached drawings.

BRIEF DESCRIPTION OF THE DRAWINGS

The accompanying drawings, which are incorporated in and constitute a part of the specification, illustrate exemplary embodiments, features, and aspects of the invention and, together with the description, serve to explain the principles of the invention.

FIGS. 1A and 1B illustrate a configuration of an appearance check apparatus according to a first exemplary embodiment of the present invention.

FIGS. 12A and 12B illustrate a configuration of an appearance check apparatus according to a second exemplary embodiment of the present invention.

DETAILED DESCRIPTION OF THE EMBODIMENTS

Figure 2:
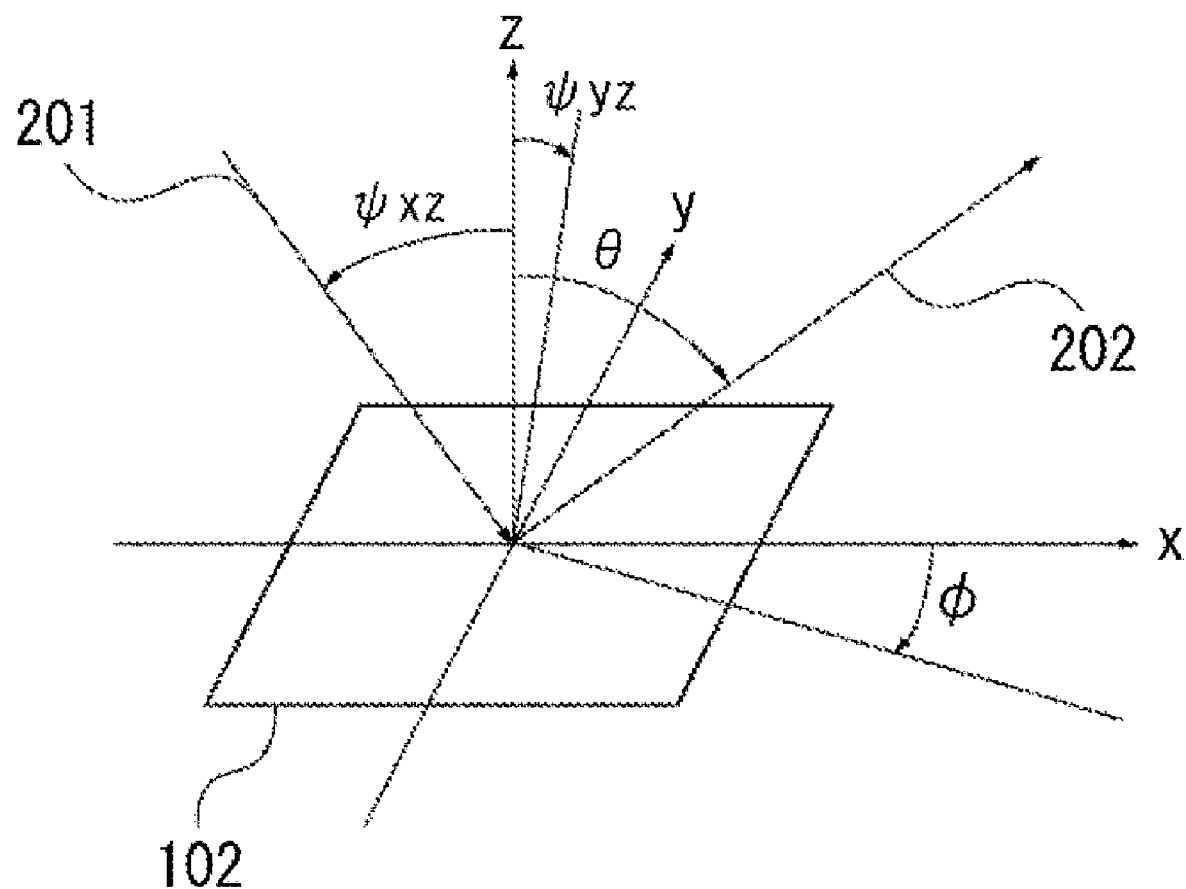
FIG. 2 illustrates a relation between an angle of illumination light emitted by an illumination unit and an angle of reflected light from an inspection target surface.

Various exemplary embodiments, features, and aspects of the invention will be described in detail below with reference to the drawings.

First Exemplary Embodiment

FIGS. 1A and 1B illustrate a configuration of an appearance check apparatus according to a first exemplary embodiment of the present invention. FIG. 1A illustrates an elevation view of an appearance check apparatus, and FIG. 1B illustrates a side view of an appearance check apparatus.

An inspection target 101 is an object to be appearance-checked. As illustrated in FIGS. 1A and 1B, the inspection target 101 in the present exemplary embodiment includes a cylindrical portion.

Referring to FIG. 1, a central axis of the cylindrical portion of the inspection target 101 is set as an x-axis, a horizontal radial direction with respect to the central axis is set as a y-axis, and a vertical radial direction with respect to the central axis is set as a z-axis.

A concrete example of a cylindrical inspection target is a charging roller. A charging roller is included in an apparatus such as a copying machine and used to transfer toner onto a copy paper. A scratch on the surface of the charging roller can have an adverse effect on an image formed on a copy paper. Therefore, a plurality of types of inspection is necessary in performing surface inspection of a charging roller to ensure high image quality.

An inspection target surface 102 is a surface to be inspected on the inspection target 101.

An illumination unit 103 irradiates the inspection target 101 with illumination light. A condition of the inspection target surface 102 can be clearly detected by irradiating the inspection target 101 with illumination light.

A point light source 104 mounted on the illumination unit 103 emits illumination light. A light bulb, halogen lamp, or a spherical stroboscopic Xe tube can be used as the point light source 104. The spherical stroboscopic Xe tube is suitable for surface inspection.

A lens 105 mounted on the illumination unit 103 collects illumination light emitted from the point light source 104 and converts the collected light into parallel light.

An imaging unit 106 captures an image of the inspection object surface 102 which is irradiated by the illumination unit 103 and acquires a captured image. The imaging unit 106 includes a photoelectric conversion area sensor unit such as a charge-coupled device (CCD) or a complementary metal-oxide semiconductor (CMOS). The imaging unit 106 further includes a lens that forms an image of an inspection target surface on the surface of the photoelectric conversion area sensor. The imaging unit 106 can also include the illumination unit 103.

In the present exemplary embodiment, an image capturing angle of the imaging unit 106 is 0° with respect to the inspection object surface 102. That is, an optical axis of an imaging surface of the imaging unit 106 is disposed perpendicular to the inspection target surface 102 to reduce image distortion and an in-focus range that occur when the imaging unit 106 captures an image from an angle. As a result, a specular reflection of illumination light from the illumination unit 103 occurs in a perpendicular direction of the imaging surface of the imaging unit 106. However, the present exemplary embodiment is not limited to image capturing in a perpendicular direction.

Further, according to the present exemplary embodiment, since the inspection target 101 includes a cylindrical portion that has a curvature, it is desirable to use an imaging unit 106 whose depth of field is large. If an image is to be captured without blurring the periphery of the cylinder, the depth of field is required to be at least r/2 when the radius of the cylinder is r.

A control unit 107 controls an image capturing operation of the imaging unit 106 and an illumination operation of the illumination unit 103, and performs image processing on a captured image acquired by the imaging unit 106. The control unit 107 includes a central processing unit (CPU), a random access memory (RAM), and a read-only memory (ROM) that stores programs for performing each process. The control unit 107 is electrically connected to the imaging unit 106 and the illumination unit 103.

The programs stored in the ROM of the control unit 107 include programs for controlling the image capturing operation of the imaging unit 106 and the illumination operation of the illumination unit 103, and a program for performing image processing on an image captured by the imaging unit 106. A part of the above-described configuration of the appearance check apparatus can be substituted by a general personal computer.

FIG. 2 illustrates a relation between an angle of illumination light emitted by the illumination unit 103 and an angle of reflected light from an inspection target surface 102. Similar to the coordinate system of FIGS. 1A and 1B, a central axis of the inspection target 101 is set as an x-axis, a horizontal radial direction with respect to the central axis is set as a y-axis, and a vertical radial direction with respect to the central axis is set as a z-axis.

An illumination light 201 is illumination light that is emitted by the illumination unit 103.

A reflected light 202 is a reflection light of the illumination light 201 from the inspection target surface 102.

$\psi_{xz}$ is an angle of the illumination light 201 in the xz plane.
$\psi_{yz}$ is an angle of the illumination light 201 in the yz plane.
$\theta$ is an angle of the reflected light 202 in the xz plane.
$\Phi$ is an angle of the reflected light 202 in the xy plane.

As described above, in a case of a three-dimensional space, an incident angle of the illumination light 201 and a reflection angle of the reflected light 202 can both be represented by two angles respectively. However, in the description below, inclination in planes other than the xz plane is assumed to be 0 for ease of description, so that processes will be performed without taking into account planes other than the xz plane. A case where planes other than the xz plane are considered will be described later.

Figure 3:
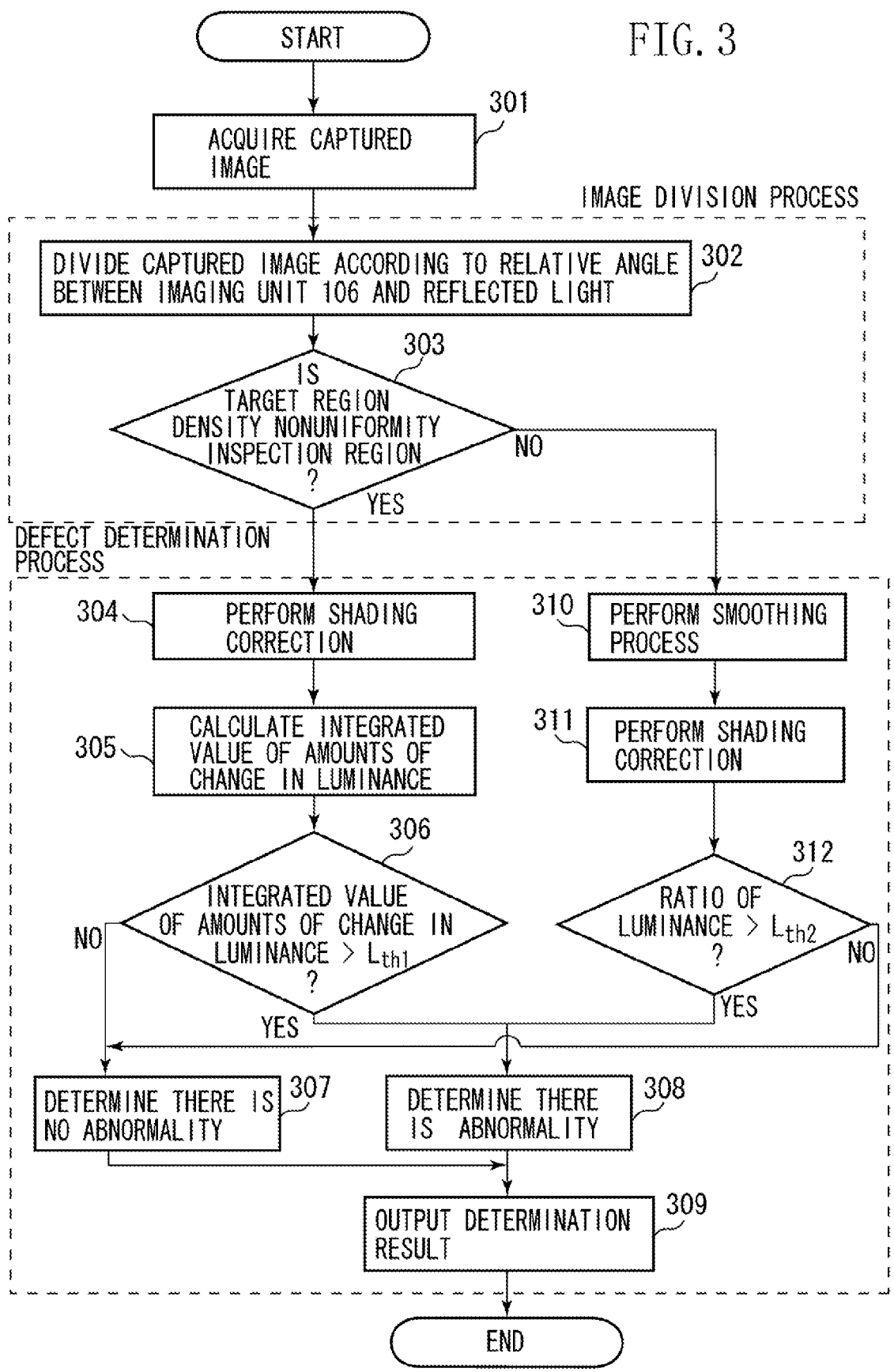
FIG. 3 is a flowchart illustrating a process according to a first exemplary embodiment of the present invention.

FIG. 3 is a flowchart illustrating a process according to the present exemplary embodiment which will be described below.

In step 301, the imaging unit 106 captures an image of the inspection target surface 102, and the control unit 107 functions as a captured image acquiring unit and acquires the captured image. The control unit 107 controls number of images to be taken and timing of capturing according to a preset image capturing parameter. A method of capturing a single captured image and performing surface inspection will be described below.

In step 302, the control unit 107 functions as an image acquiring unit and acquires inspection regions from the captured image acquired in step 301. The acquiring process in the present exemplary embodiment acquires an appropriate region for a plurality of types of inspection from the captured image. In the present exemplary embodiment, two types of inspection are performed. One type of inspection is a density nonuniformity inspection for detecting minute unevenness (i.e., a first surface shape for a first surface inspection) on the inspection target surface 102. Another type of inspection is a defective site inspection for detecting a defect that has a comparatively large surface shape, such as a scratch or dust adherence (i.e., a second surface shape for a second surface inspection) on the inspection target surface 102. However, the present invention is not limited to the two types of inspection, and can also be applied to three or more types of inspection.

Figure 4:
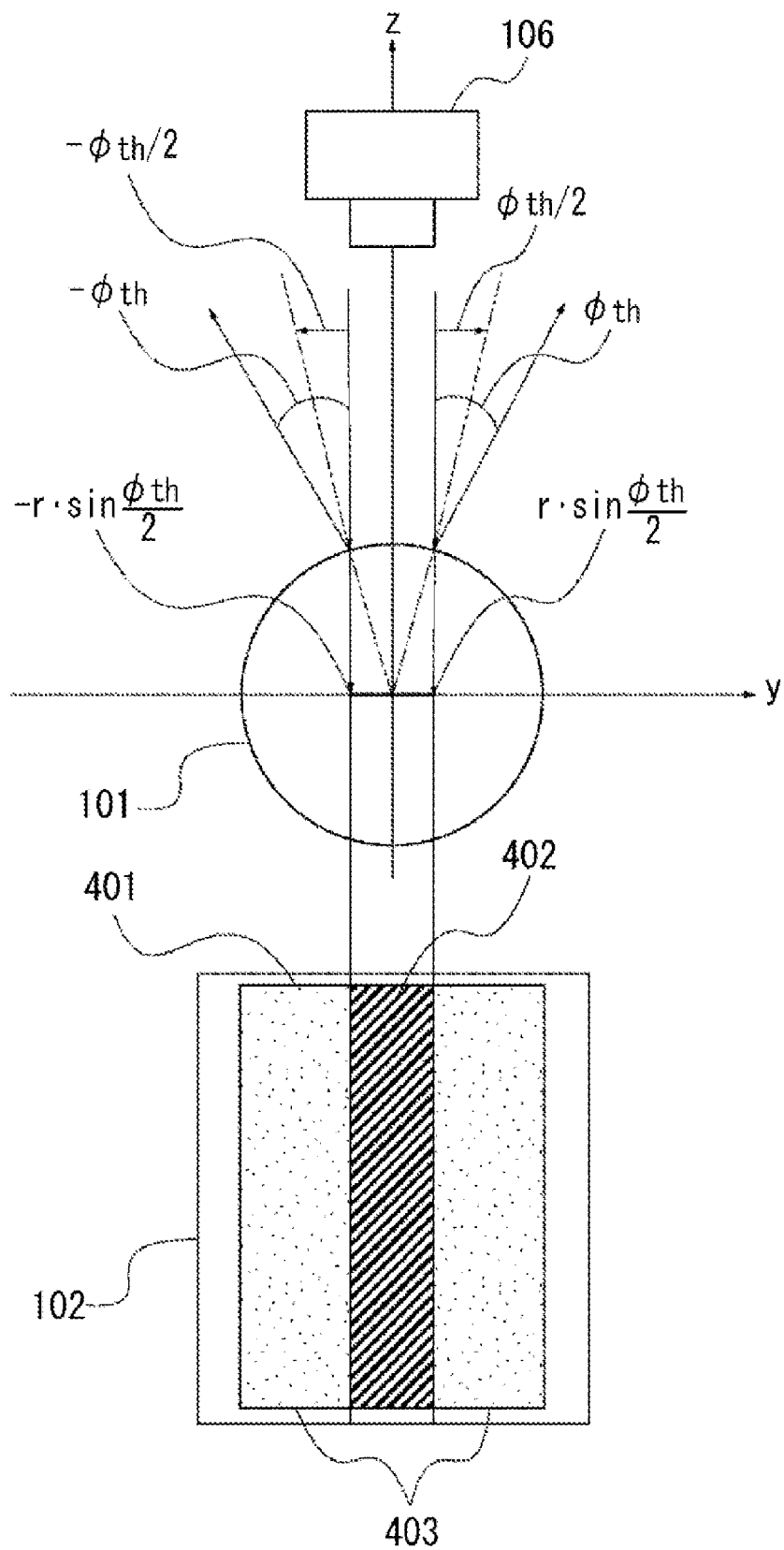
FIG. 4 illustrates a density nonuniformity inspection region and a defective site inspection region according to a first exemplary embodiment of the present invention.

FIG. 4 illustrates a density nonuniformity inspection region and a defective site inspection region according to a first exemplary embodiment of the present invention. As described above, in the present exemplary embodiment, the inspection target 101 including a cylindrical portion will be inspected. The capture image acquired by the imaging unit 106 becomes a rectangular region such as a captured image 401.

Referring to FIG. 4, a region in the proximity of an origin on the y-axis in the captured image 401 is a region which is approximately perpendicular with respect to the imaging surface of the imaging unit 106. In such a region in the proximity of the origin on the y-axis, a portion of reflected light of the illumination light caused by the first surface shape and emitted by the illumination unit 103 that is more than that caused by the second surface shape is diffuse-reflected light caused by minute unevenness. Since there is only a small amount of reflected light other than specular-reflected light in a luminance distribution of diffuse-reflected light caused by minute unevenness, such a diffuse-reflected light is close to specular-reflected light. The luminance distribution of diffuse-reflected light caused by minute unevenness is thus more prominent in the region in the proximity of the origin on the y-axis. Therefore, the region in the proximity of the origin on the y-axis is acquired as a density nonuniformity inspection region 402 (i.e., a first image region).

A diffuse-reflected light is reflected light that corresponds to a surface shape of an illuminated object. In general, light which is diffused in a direction other than a specular reflection direction increases as the surface shape becomes more complex.

Since the inspection target surface 102 is curved, diffuse-reflected light caused by minute unevenness which is close to specular-reflected light hardly appears in regions of the captured image 401, which are distant from the origin on the y-axis. On the other hand, a portion of diffuse-reflected light caused by a scratch and the second surface shape or adhering dust that is more than that caused by the first surface shape is reflected in a direction other than the specular reflection direction. The proportion of diffuse-reflected light caused by the scratch or adhering dust thus increases in a region that is distant from the origin on the y-axis.

Therefore, a defective site due to a scratch or dust adherence can be easily extracted in a region that is distant from the origin on the y-axis. The region which is distant from the origin on the y-axis is thus acquired as a defective site inspection region 403 (i.e., a second image region).

Intensity distributions of reflected light with respect to an incident angle of the illumination light are different in the first image region and the second image region. As a result, a different surface inspection process can be performed in each of the regions.

As described above, the density nonuniformity inspection region 402 and the defective site inspection region 403 can be acquired from a single captured image using relative positions such as the position of the imaging unit 106 and the inclination of the inspection target surface 102.

In practice, a threshold value for dividing the regions is necessary to acquire the density nonuniformity inspection region 402 and the defective site inspection region 403. In the present exemplary embodiment, a range of a region is calculated using a radius r of the cylinder in the inspection target 101 and a threshold value $\Phi_{th}$. $\Phi_{th}$ is an angle between illumination light and reflected light at which a proportion of diffuse-reflected light caused by minute unevenness and diffuse-reflected light caused by a scratch or dust adherence is switched when illumination light is irradiated perpendicularly onto the inspection target surface 102. In the present exemplary embodiment, the control unit 107 functions as a threshold value acquiring unit and acquires the threshold value $\Phi_{th}$.

In the present exemplary embodiment, the density nonuniformity inspection region 402 is defined as a region between $-r \cdot \sin \Phi_{th}/2$ to $r \cdot \sin \Phi_{th}/2$ with reference to the y-axis, based on an empirical rule. The defective site inspection region 403 is a region other than the density nonuniformity inspection region 402. A range of a region to be acquired can be changed as appropriate, according to the relative positions such as a position of the imaging unit 106, an incident angle of illumination light emitted by the illumination unit 103 and a shape of the inspection target 101. The control unit 107 functions as necessary as an information acquiring unit which acquires information about the inspection target surface 102 and a position acquiring unit which acquires a position of the illumination unit 103. A method of acquiring $\Phi_{th}$ used as a threshold value will be described below.

In step 303, the control unit 107 determines whether a target region in the captured image is the density nonuniformity region 402 and causes a process to branch. A target region is determined based on a user instruction or a preset parameter. If the entire captured image is the target region, density nonuniformity inspection and defective site inspection are parallelly-performed. Since the captured image is divided into the density nonuniformity region 402 and the defective site inspection region 403 in step 302, it can be easily determined whether the target region is the density nonuniformity region 402. If the target region is the density non uniformity region 402 (YES in step 303), the process proceeds to step 304. On the other hand, if the target region is not the density nonuniformity region 402 (NO in step 303), the process proceeds to step 310.

In step 304, the control unit 107 performs a shading correction on the image of the target region set in step 303. The shading correction is a process of correcting luminance unevenness due to a characteristic of the imaging unit 106. A number of imaging elements are disposed in the imaging unit 106 to acquire an image, and it is desirable that the characteristics of each of the imaging elements are similar. However, the characteristics are actually different each other due to manufacturing processes. The shading correction is a process of correcting the differences in the characteristics of the imaging elements using image processing by previously acquiring the differences in the characteristics of the imaging elements. After performing the shading correction in step 304, the process proceeds to step 305.

In step 305, the control unit 107 calculates an integrated value of amounts of change in luminance in the target region.

In a case where there is a great number of minute unevenness in the subject region, an amount of luminance unevenness caused by the minute unevenness becomes large in a captured image. In the present exemplary embodiment, a difference in luminance values is calculated to detect the amount of luminance unevenness. A small region is set for each of the pixels in the target region, and a difference between a minimum value and a maximum value of luminance in the small region is calculated. The difference of luminance in a small region is then calculated for all pixels in the target region, and the difference values are integrated. If the calculated integrated value is greater than a predetermined value, it can be determined that the amount of luminance unevenness is large in the target region. After calculating the integrated value of amounts of change in luminance, the process proceeds to step 306.

In step 306, the control unit 107 functions as a surface inspection processing unit, and determines whether the integrated value of amounts of change in luminance calculated in step 305 is greater than a predetermined value $L_{th1}$. If the integrated value of the amounts of change in luminance is greater than $L_{th1}$ (YES in step 306), the process proceeds to step 308. If the integrated value of the amounts of change in luminance is not greater than $L_{th1}$ (NO in step 306), the process proceeds to step 307. The predetermined value $L_{th1}$ can be appropriately obtained by comparing an integrated value of amounts of change in luminance of a sample in which there is a great number of minute unevenness, and an integrated value of amounts of change in luminance of a sample in which there is no minute unevenness.

In step 307, the control unit 107 determines that there is no abnormality, and the process proceeds to step 309.

In step 308, the control unit 107 determines that there is abnormality, and the process proceeds to step 309.

In step 309, the control unit 107 outputs a determination result according to the determination result of step 307 or step 308. The control unit 107 displays a message indicating that there is abnormality or that there is no abnormality on an image display unit such as a monitor.

In step 310, the control unit 107 functions as a smoothing unit and performs a smoothing process on the target region of the captured image. A smoothing process is a process in which an average value of surrounding pixel values is calculated for each pixel, and a pixel value of each pixel is converted to the average value. As a result of performing the smoothing process, minor luminance unevenness is reduced, and it becomes easier to detect a comparatively large defect such as a scratch or dust adherence in the defective site inspection region 403. After performing the smoothing process, the process proceeds to step 311.

In step 311, the control unit 107 performs a shading correction on the target region of the captured image. The shading correction process performed in step 311 is similar to the process performed in step 304, and further description will be omitted.

In step 312, the control unit 107 functions as a surface inspection unit. The control unit 107 determines whether a ratio between a luminance value of a region in which there is a scratch or dust adherence and a luminance value of a region in which there is no scratch or dust adherence is greater than or equal to a predetermined value $L_{th2}$.

Since there are various image processing methods to separate a region in which there is a scratch or dust adherence from a region in which there is no scratch or dust adherence, description will be omitted. A predetermined value $L_{th2}$ in the present exemplary embodiment can be appropriately obtained by comparing a luminance value of a sample in which there is a scratch or dust adherence with a luminance value of a sample in which there is no scratch or dust adherence. If the ratio of luminance values is greater than the predetermined value $L_{th2}$ (YES in step 312), the process proceeds to step 308. On the other hand, if the ratio of luminance values is not greater than the predetermined value $L_{th2}$ (NO in step 312), the process proceeds to step 307.

If a plurality of types of surface inspection is to be performed simultaneously in a conventional technique, a plurality of illumination lights with different illumination angles or a plurality of imaging units with different viewing angles is necessary. However, according to the present exemplary embodiment, a plurality of types of surface inspection can be performed using a captured image obtained by a single imaging unit and a single illumination unit by performing the above-described process. Since the present exemplary embodiment only requires a single imaging unit and a single illumination unit, a configuration of an appearance check apparatus can be simplified, and manufacturing cost of the appearance check apparatus can be reduced.

In the present exemplary embodiment, a surface inspection using a single captured image is performed. However, a surface inspection can be performed using, for example, a driving unit (not illustrated) which rotates the inspection target 101 around a central axis of the cylindrical portion to acquire a plurality of captured images at every predetermined angle. Density nonuniformity inspection and defective site inspection can be performed on the entire surface of the inspection target surface 102 by performing surface inspection using a plurality of captured images acquired at every predetermined angle. In such a case, since a range that can be detected by one image capturing is limited by the threshold value $\Phi_{th}$, it is necessary that a pitch of a rotation angle in capturing images is smaller than $\Phi_{th}$.

As described above, an appearance check apparatus requires only a single imaging unit and a single illumination unit even in a case where a plurality of captured images is acquired. Therefore, the manufacturing cost of the appearance check apparatus can be reduced.

Further, in the present exemplary embodiment, surface inspection targets are defective surface shapes including minute unevenness and defects such as a scratch or dust adherence. However, a proportion of specular-reflected light changes according to a material which configures an inspection target surface or according to transmittance of illumination light with which the inspection target surface is irradiated. Therefore, the method described in the present exemplary embodiment can be applied to various surface inspections.

Further, in the present exemplary embodiment, a threshold value $\Phi_{th}$ and relative positions of an imaging unit and the inspection target are used in separating the density nonuniformity inspection region from the defective site inspection region. However, if the relative positions are previously known, a region in which a luminance value is larger can be determined as a density nonuniformity inspection region, and a region in which a luminance value is smaller can be determined as a defective site inspection region in the captured image. The image can be thus divided into the two regions.

A method of obtaining the threshold value $\Phi_{th}$ used in step 302 will be described below.

Figure 5A:
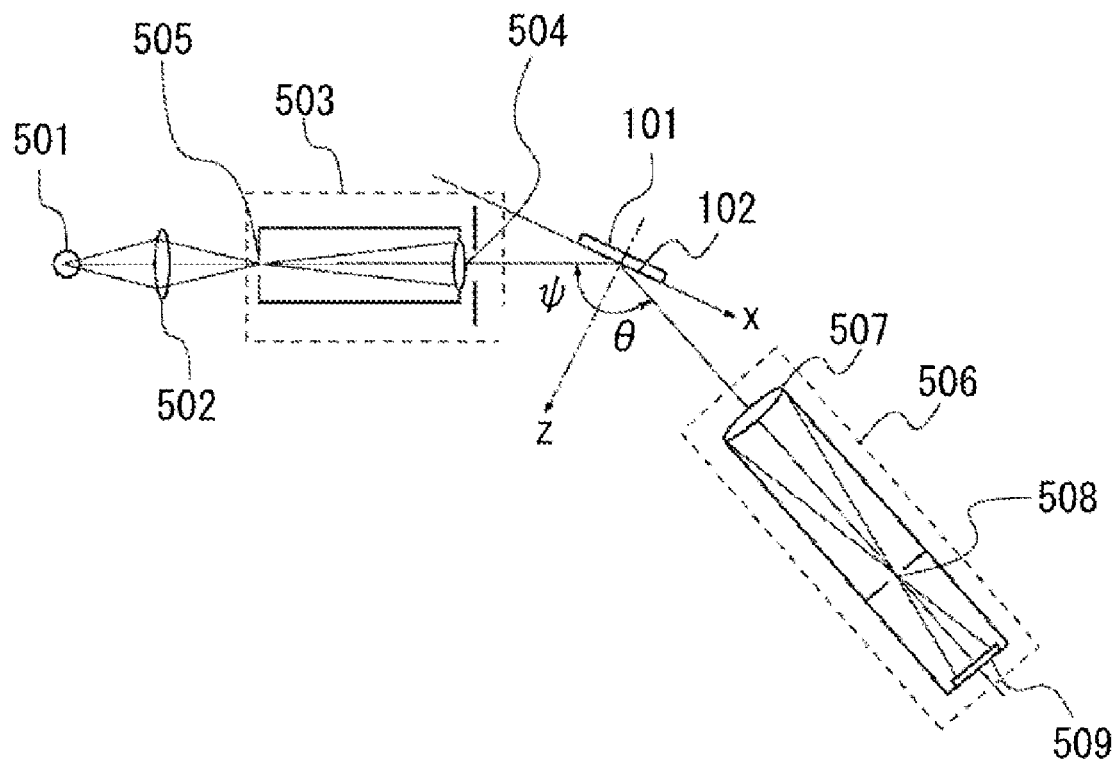
FIGS. 5A and 5B illustrate a configuration of a goniophotometer.
Figure 5B:
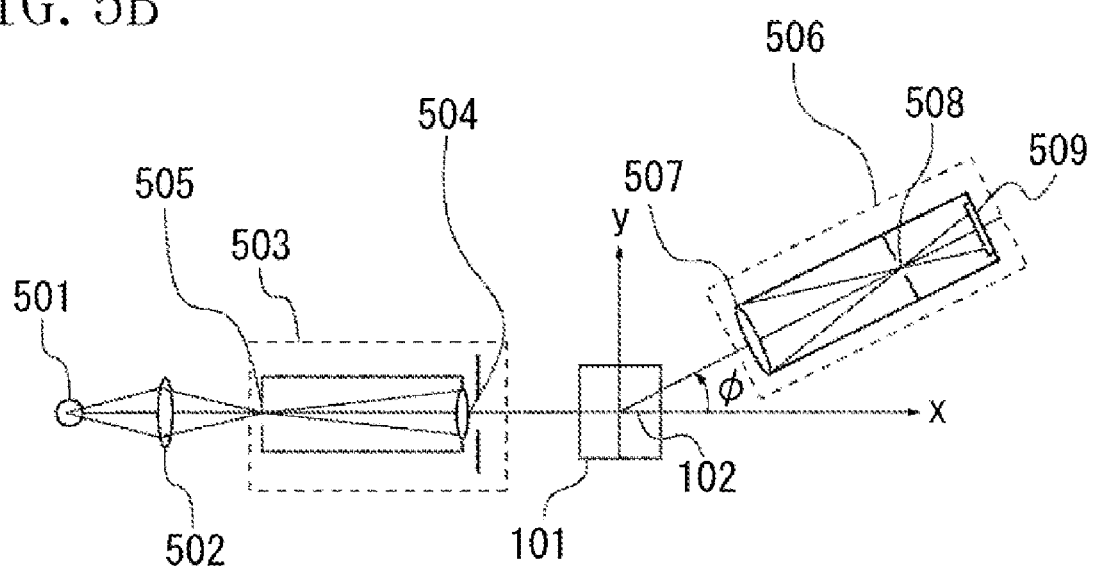

FIGS. 5A and 5B illustrate a configuration of a gonio-photometer for obtaining the threshold value $\Phi_{th}$ in the present exemplary embodiment. FIG. 5A illustrates a gonio-photometer in an xz plane, and FIG. 5B illustrates a gonio-photometer in a xy plane.

A point light source 501 disposed in a gonio-photometer emits illumination light.

A collective lens 502 is a convex lens which collects illumination light emitted by the point light source 501.

A collimator 503 converts the illumination light collected by the collective lens 502 into parallel light.

A collimator lens 504 is a convex lens disposed in the collimator 503.

A slit 505 is a groove formed on a focal position of the collimator lens 504. The illumination light emitted by the point light source 501 enters the collimator 503 through the slit 505. The illumination light entering the collimator 503 is emitted to the outside through the collimator lens 504, so that the illumination light is converted substantially to parallel light. The converted illumination light falls on the inspection target surface 102 and is reflected from the inspection target surface 102.

A light-receiving unit 506 receives the reflected light from the inspection target surface 102.

A light-receiving lens 507 is a convex lens disposed in the light-receiving unit 506 which collects reflected light.

A slit 508 is formed on a focal position of the light-receiving lens 507 and performs a reverse function of the slit 505.

A photoelectric conversion element 509 disposed on the light-receiving unit 506 generates an electric current according to an intensity of the reflected light received through the slit 508. The intensity of the reflected light can be thus measured by the electric current generated by the photoelectric conversion element 509.

The collimator 503 and the light-receiving unit 506 are driven by a driving unit (not illustrated), and relative angles $\Psi_{xy}$, θ, Φ can be changed to various angles. In FIGS. 5A and 5B, $\Psi_{xz}$ is used as the relative angle of the collimator. However, $\Psi_{yz}$ can be also used.

The relative angles $\Psi_{xz}$, θ and Φ are changed using the driving unit and the intensity distribution of reflected light is measured. Thus, an angle $\Phi_{th}$ at which the proportion of the diffuse-reflected light caused by minute unevenness and the diffuse-reflected light caused by scratch or dust adherence is switched, can be estimated.

$\Phi_{th}$ can be estimated, for example, by using a gonio-photometer and acquiring luminance of diffuse-reflected light from various angles of a sample in which there is only a scratch or dust adherence. The gonio-photometer is then used to acquire luminance of diffuse-reflected light from various angles of a sample in which there is only minute unevenness. As a result of the above processes, a distribution of diffuse-reflected light caused by a scratch or dust adherence and a distribution of diffuse-reflected light caused by minute unevenness can be acquired. The acquired diffuse-reflected light distributions are then superposed, so that a point at which the proportion is switched can be obtained. The angle $\Phi_{th}$ can be thus estimated.

Figure 6:
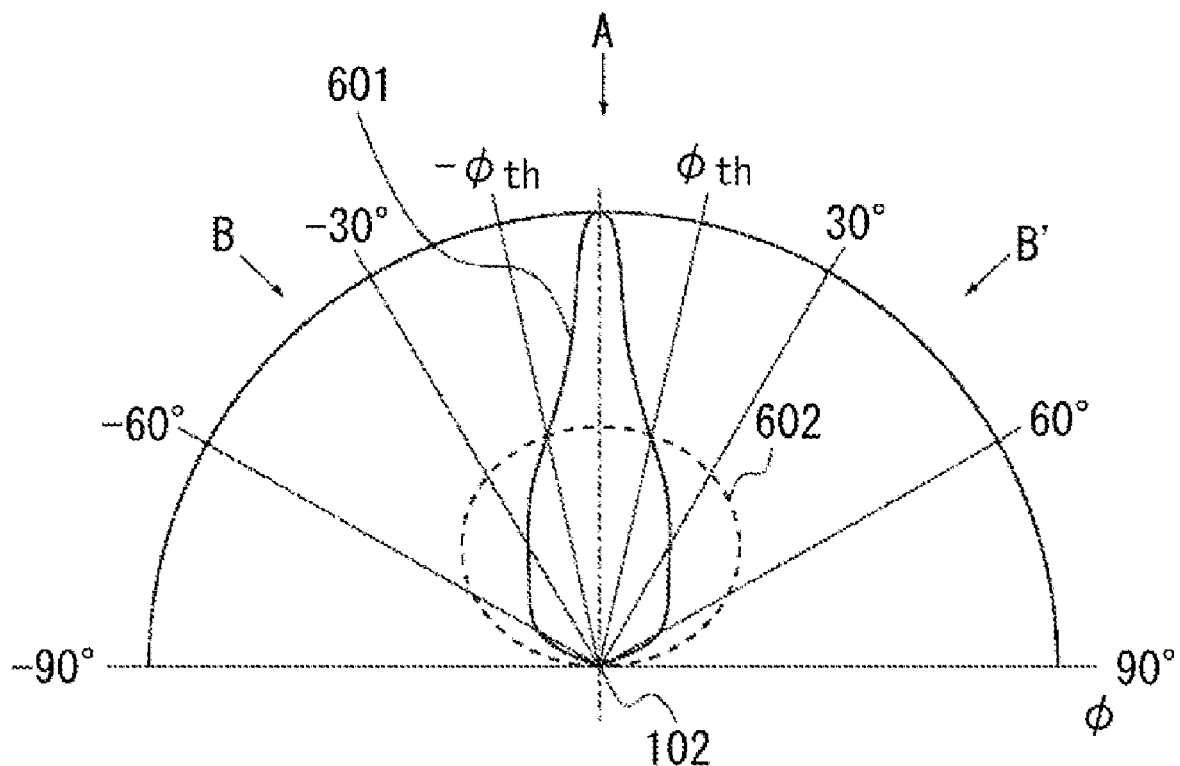
FIG. 6 illustrates proportions of diffuse-reflected light caused by minute unevenness to diffuse-reflected light caused by a scratch or adhering dust.

FIG. 6 is a schematic diagram illustrating the proportion of diffuse-reflected light caused by minute unevenness and diffuse-reflected light caused by scratches or dust adherence. FIG. 6 illustrates a measurement result of diffuse-reflected light by causing proximate parallel light to fall on a surface at a predetermined incident angle $\Psi_{xz}$, and changing Φ. Since an optical axis of a camera lens is set perpendicular with respect to the inspection target surface 102, θ=0°. Therefore, a diffuse-reflected light curve which is measured in the present exemplary embodiment represents an angle characteristic of a laterally-scattered light. A result of measurement in which proximate parallel light falls on a surface to be inspected at the incident angle $\Psi_{xz}$, and θ is changed can be similarly obtained.

A diffuse-reflected light curve 601 is a curve representing diffuse-reflected light caused by minute unevenness when illumination light is irradiated in a direction perpendicular to the inspection target surface 102. A diffuse-reflected light curve is a curve that represents change in the intensity of luminance of diffuse-reflected light according to an irradiation angle, when light is incident from a predetermined direction. In general, a diffuse-reflected light curve of a reflected light varies in accordance with a surface shape and a surface member of the inspection target surface 102.

A diffuse-reflected light curve 602 is a curve representing diffuse-reflected light caused by a scratch or dust adherence when illumination light is irradiated in a direction perpendicular to the inspection target surface 102.

As illustrated by the diffuse-reflected light curve 601 in FIG. 6, diffuse-reflected light caused by minute unevenness is similar to specular-reflected light that is reflected at maximum luminance in a perpendicular direction. However, luminance of the diffuse-reflected light in a perpendicular direction is smaller in a peripheral part. The diffuse-reflected light curve 601 can be thus regarded as reflected light in which a proportion of specular-reflected light is large. On the other hand, as illustrated by the diffuse-reflected light curve 602 in FIG. 6, diffuse-reflected light caused by a scratch or dust adherence is diffused in nearly all directions from the inspection target surface 102. Therefore, the diffuse-reflected light curve 602 can be regarded as reflected light in which a proportion of specular-reflected light is small.

FIG. 6 illustrates that the proportion of diffuse-reflected light curve 602 becomes greater than the proportion of diffuse-reflected light curve 601 after an inclination angle in a direction perpendicular to the inspection target surface 102 passes $\Phi_{th}$. If the inspection target surface 102 is viewed from a direction A in FIG. 6, it is easy to observe minute unevenness. However, it is difficult to observe a scratch or dust adherence from direction A. On the other hand, if the inspection target surface 102 is viewed from directions B or B' in FIG. 6, it is easy to observe a scratch or dust adherence and difficult to observe minute unevenness.

Figure 7:
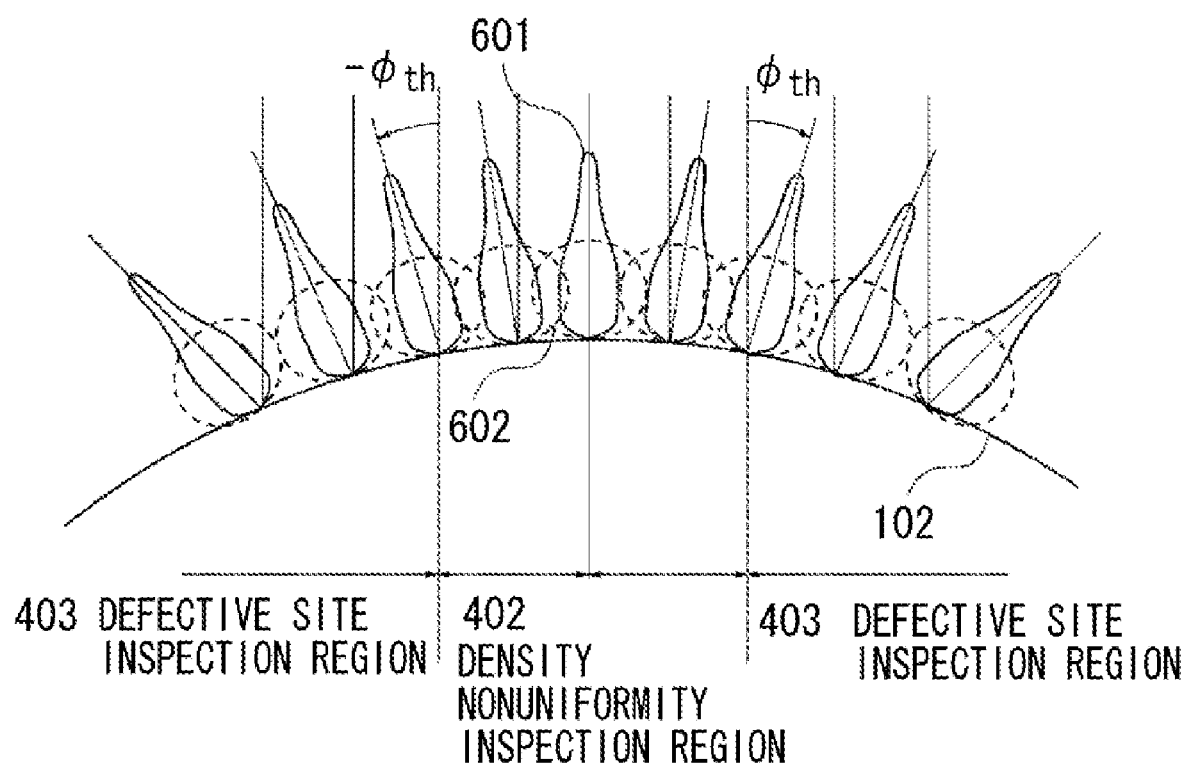
FIG. 7 illustrates a diffuse-reflected light curve of an inspection target.

FIG. 7 illustrates diffuse-reflected light curves at various positions on the inspection target surface 102. Referring to FIG. 7, a ratio of the diffuse-reflected light 601 to the diffuse-reflected light 602 changes at a position where an inclination angle of the inspection target surface 102 with respect to the perpendicular direction reaches $\Phi_{th}$. Therefore, an appropriate surface inspection can be performed if the density non-uniformity inspection region 402 and the defective site inspection region 403 are divided at the position where an inclination angle of the inspection target surface 102 with respect to the perpendicular direction reaches $\Phi_{th}$.

As described above, in the present exemplary embodiment, the density nonuniformity inspection region 402 is determined as a region from an origin on the y-axis to $-r \cdot \sin \Phi_{th}/2$ and $r \cdot \sin \Phi_{th}/2$. However, the density nonuniformity inspection region 402 can be set at a position where a relative angle between the imaging unit 106 and the reflected light from the inspection target surface 102 reaches $\Phi_{th}$, according to the curvature of the inspection target surface 102.

A process in a plane other than the xz plane will be described below.

Figures 8A, 8B:
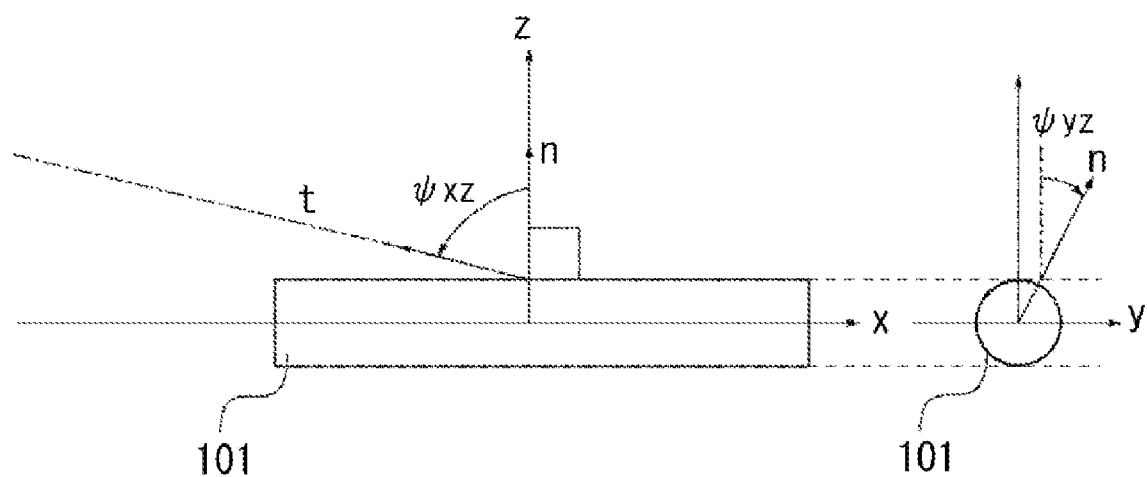
FIGS. 8A and 8B illustrate a state in which an illumination light is inclined with respect to an inspection target.

FIG. 8A illustrates a state in which an illumination light is inclined at an angle $\Psi_{xz}$ in a direction perpendicular to the inspection target 101 in an xz plane. FIG. 8B illustrates a state in which an illumination light is inclined at an angle $\Psi_{yz}$ in a direction perpendicular to the inspection target 101 in an yz plane.

Figure 9:
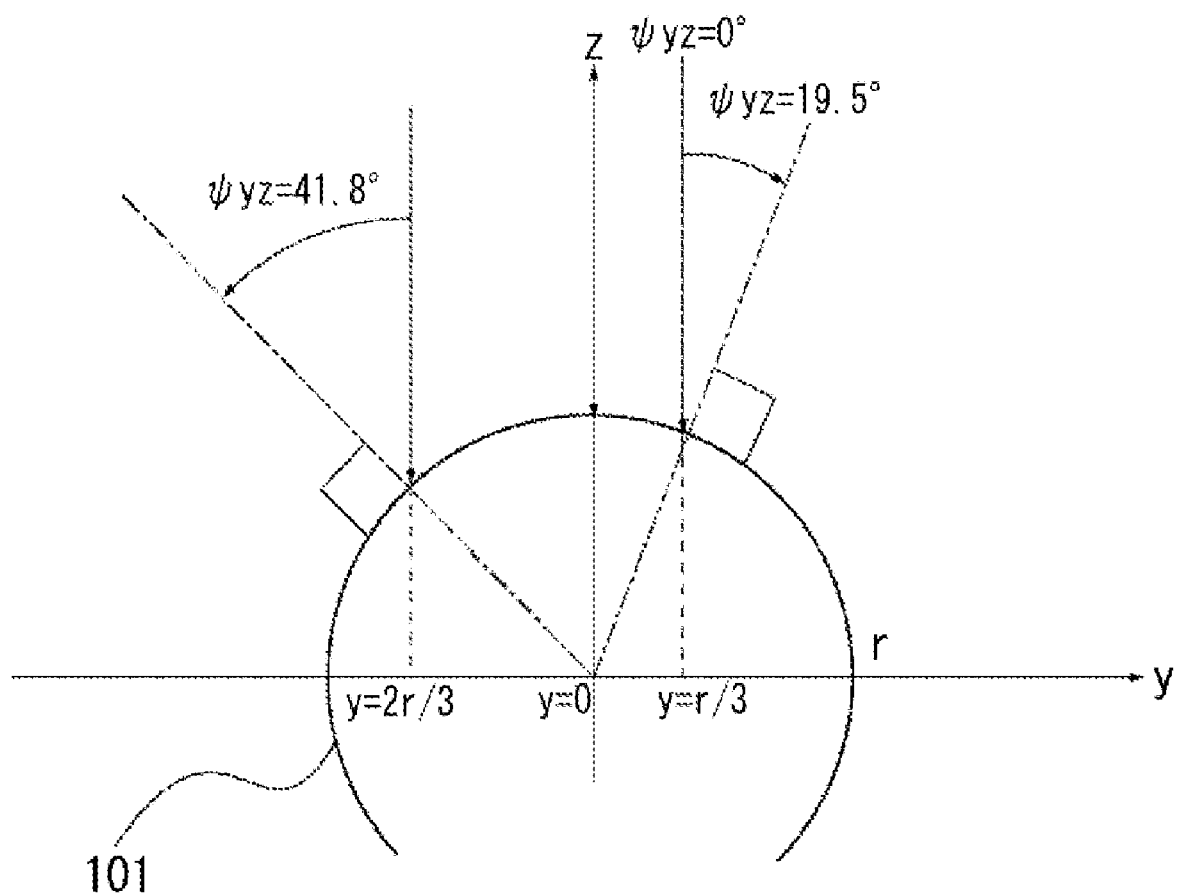
FIG. 9 illustrates a relation between coordinate position y and an inclination $\Psi_{yz}$ of an illumination light in an yz plane.

FIG. 9 illustrates a relation between y and $\Psi_{yz}$. For example, when y=0, $\Psi_{yz}$=0°. When y=r/3, $\Psi_{yz}$=19.5°, and when y=2r/3, $\Psi_{yz}$=41.8°.

The relation between y and $\Psi_{yz}$ can be described by the following equation (1).

$$\Psi_{yz} = \sin^{-1}(y/r) \quad (1)$$

Figure 10:
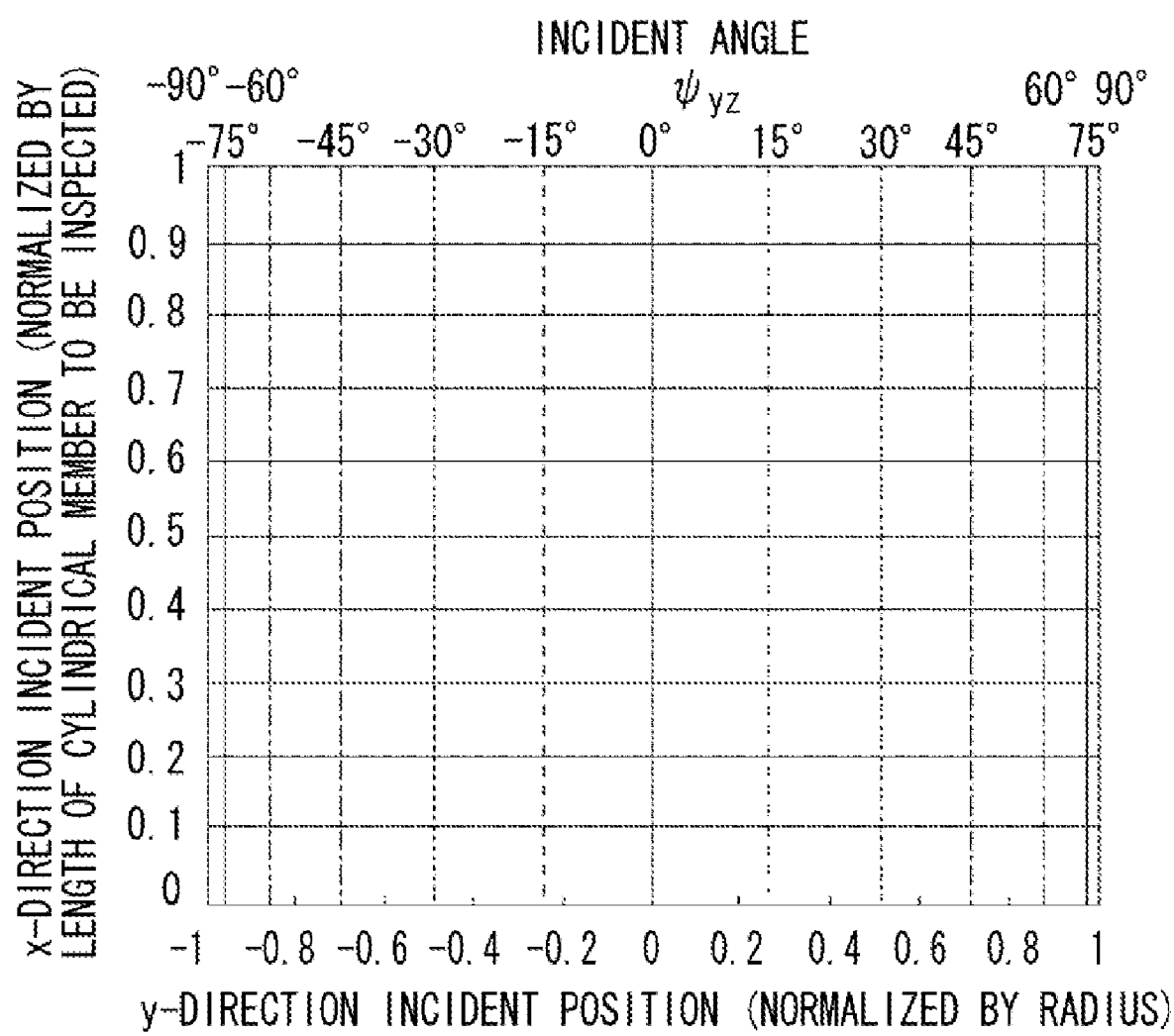
FIG. 10 is a graph which illustrates positions where an incident angle $\Psi_{yz}$ in an yz plane is equivalent.

FIG. 10 is a graph illustrating positions at which an incident angle $\Psi_{yz}$ is equivalent in the yz plane according to equation (1). In the graph, a y-direction incident position is normalized by radius r, and an x-direction incident position is normalized by length L of a cylindrical inspection member.

An incident angle $\Psi$ with respect to the inspection target 101 will be described with reference to FIGS. 8A and 8B. An incident angle of light in the xy plane will be referred to as $\Psi_{xz}$, and an incident angle of light in the yz plane will be referred to as $\Psi_{yz}$. Further, an incident direction vector of an incident light will be referred to as t, and a normal vector set on an incident surface of the incident light will be referred to as n.

The incident direction vector t can be then described by the following equation (2).

$$t = (\sin \Psi_{xz}, 0, \cos \Psi_{xz}) \quad (2)$$

On the other hand, the normal vector n can be described by the following equation (3).

$$n = (0, \sin \Psi_{yz}, \cos \Psi_{yz}) \quad (3)$$

Since the incident angle $\Psi$ is an angle between the incident direction vector t and the normal vector n, the incident angle $\Psi$ can be obtained as an inner product of t and n. Therefore, the incident angle $\Psi$ can be represented by the following equations (4) and (5).

$$\cos \Psi = t \cdot n/(|t| \cdot |n|) = \cos \Psi_{xz} \cdot \cos \Psi_{yz} \quad (4)$$

$$\Psi = \cos^{-1}(\cos \Psi_{xz} \cdot \cos \Psi_{yz}) \quad (5)$$

Figure 11:
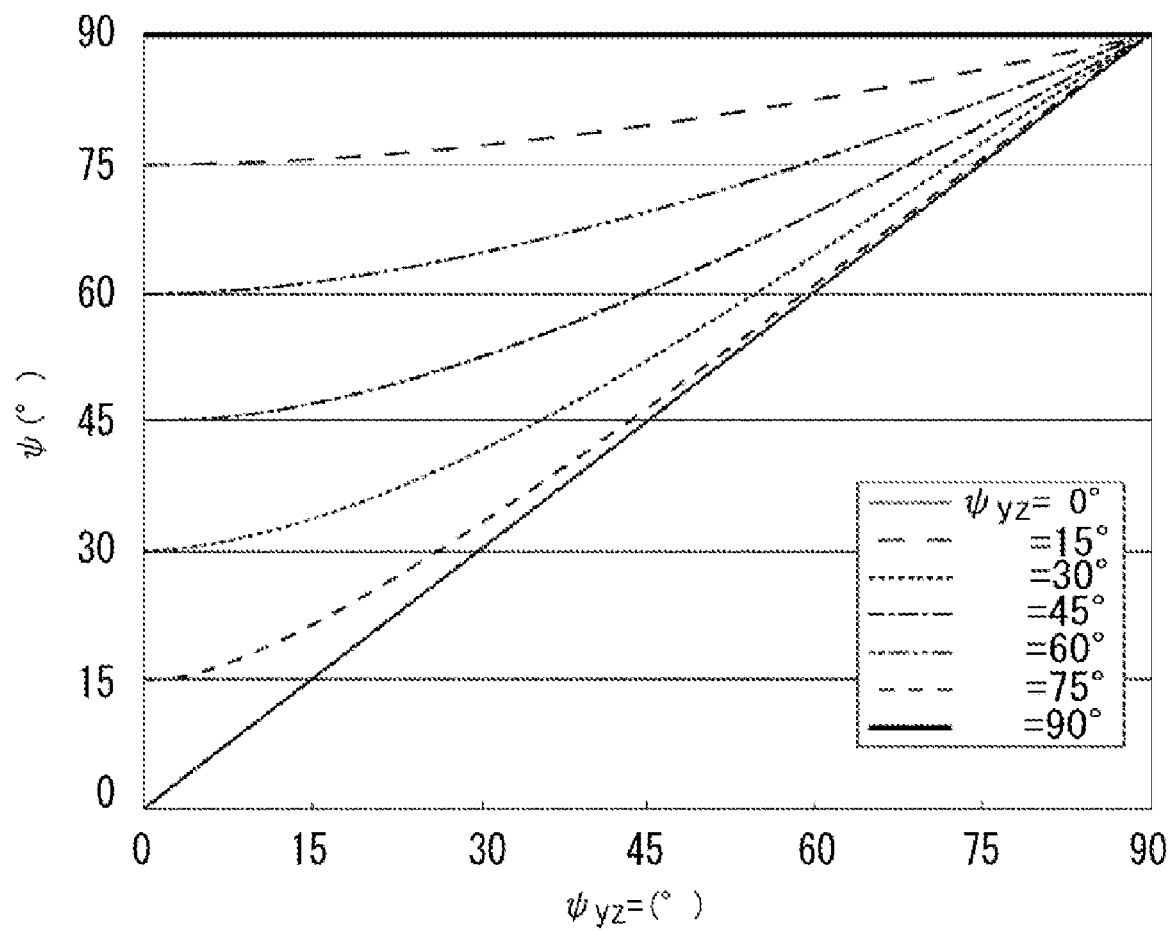
FIG. 11 illustrates a graph in which $\Psi_{xz}$ is plotted at every 15° between 0° and 90° where $\Psi$ is set as a vertical axis and $\Psi_{yz}$ as a horizontal axis.

FIG. 11 illustrates a graph in which $\Psi_{xz}$ is plotted at every 15° from 0° to 90°, by setting $\Psi$ as the vertical axis and $\Psi_{yz}$ as the horizontal axis.

When $\Psi_{xz} = 0°$, the difference between $\Psi$ and $\Psi_{yz}$ is 0. The difference increases as $\Psi_{xz}$ increases, and the difference is greatest when $\Psi_{xz} = 90°$. By using the graph illustrated in FIG. 11, $\Psi$ can be easily obtained, so that a process which takes into account planes other than the xz plane can be performed.

Second Exemplary Embodiment

FIGS. 12A and 12B illustrate a configuration of an appearance check apparatus according to a second exemplary embodiment of the present invention. The configuration of the appearance check apparatus is similar to the first exemplary embodiment. An inspection target is different between the first and second exemplary embodiments.

An inspection target 1201 includes a spherical portion. A specific example of a spherical shape is a convex lens.

An inspection target surface 1202 is a surface of the inspection target 1201 that is in a shape of a convex lens.

A center line 1203 runs through the center of the inspection target 1201.

In a case where proximate parallel light is irradiated on the inspection target 1201 including a spherical portion, an incident angle $\Psi_{yz}$ changes according to an x-direction incident position and a y-direction incident position.

Figure 13:
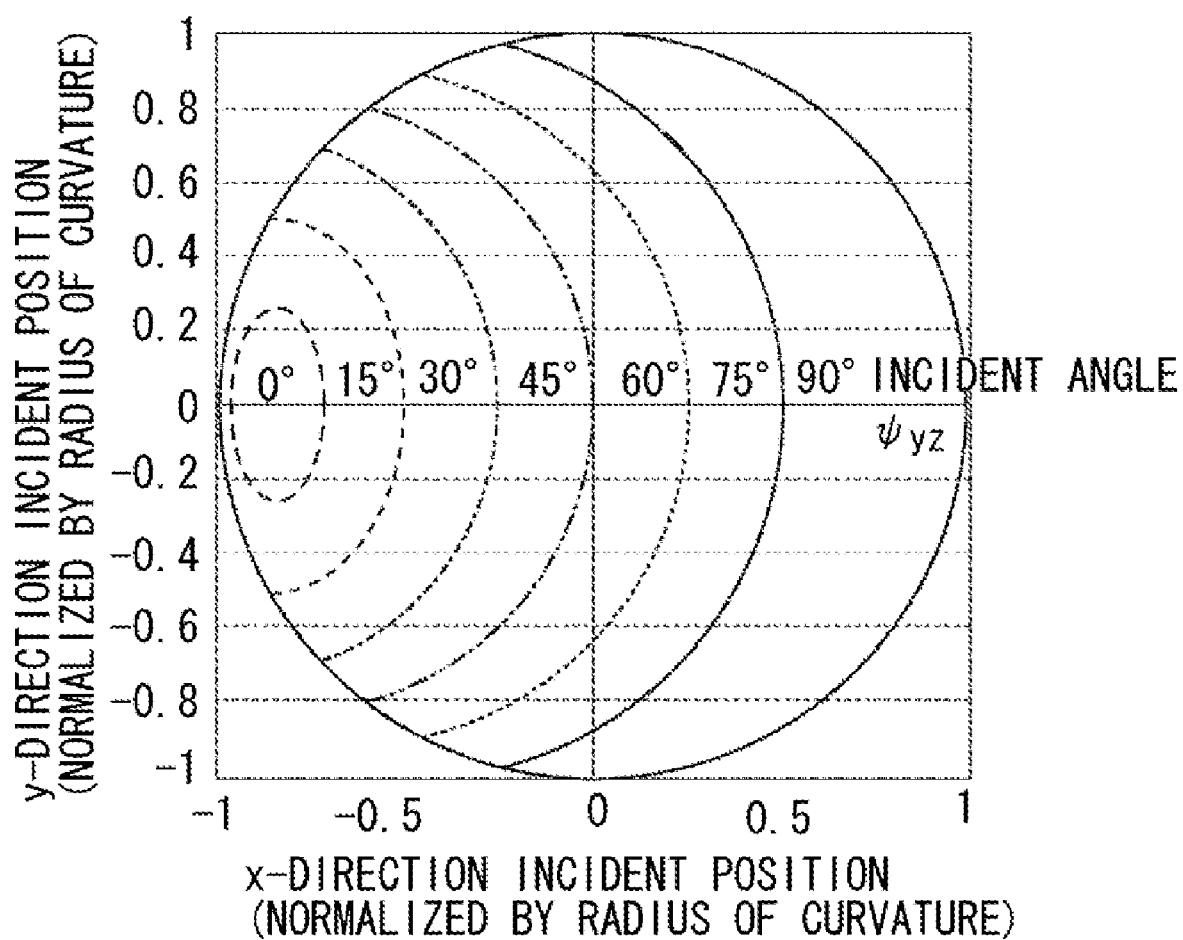
FIG. 13 is a graph illustrating curves in which an incident angle $\Psi_{yz}$ is equivalent when light is emitted at an oblique incident angle $\Psi_{xz}=60°$.

FIG. 13 is a graph illustrating curves in which the incident angle $\Psi_{yz}$ is equivalent when light is obliquely incident at an incident angle of $\Psi_{xz} = 60°$. A process which takes into account planes other than the xz plane can be performed by using the graph illustrated in FIG. 13, similar to the first exemplary embodiment.

The process of dividing a captured image region into the density nonuniformity inspection region 402 and the defective site inspection region 403 is similar to the process with reference to FIG. 3 in the first exemplary embodiment. Therefore, description will be omitted.

In the first exemplary embodiment, the inspection target 101 is rotated by a driving unit to perform inspection on the entire surface of the inspection target surface 102. Also in the present exemplary embodiment, the inspection target 1201 is moved to inspect the entire surface of the inspection target surface 102.

Figure 14:
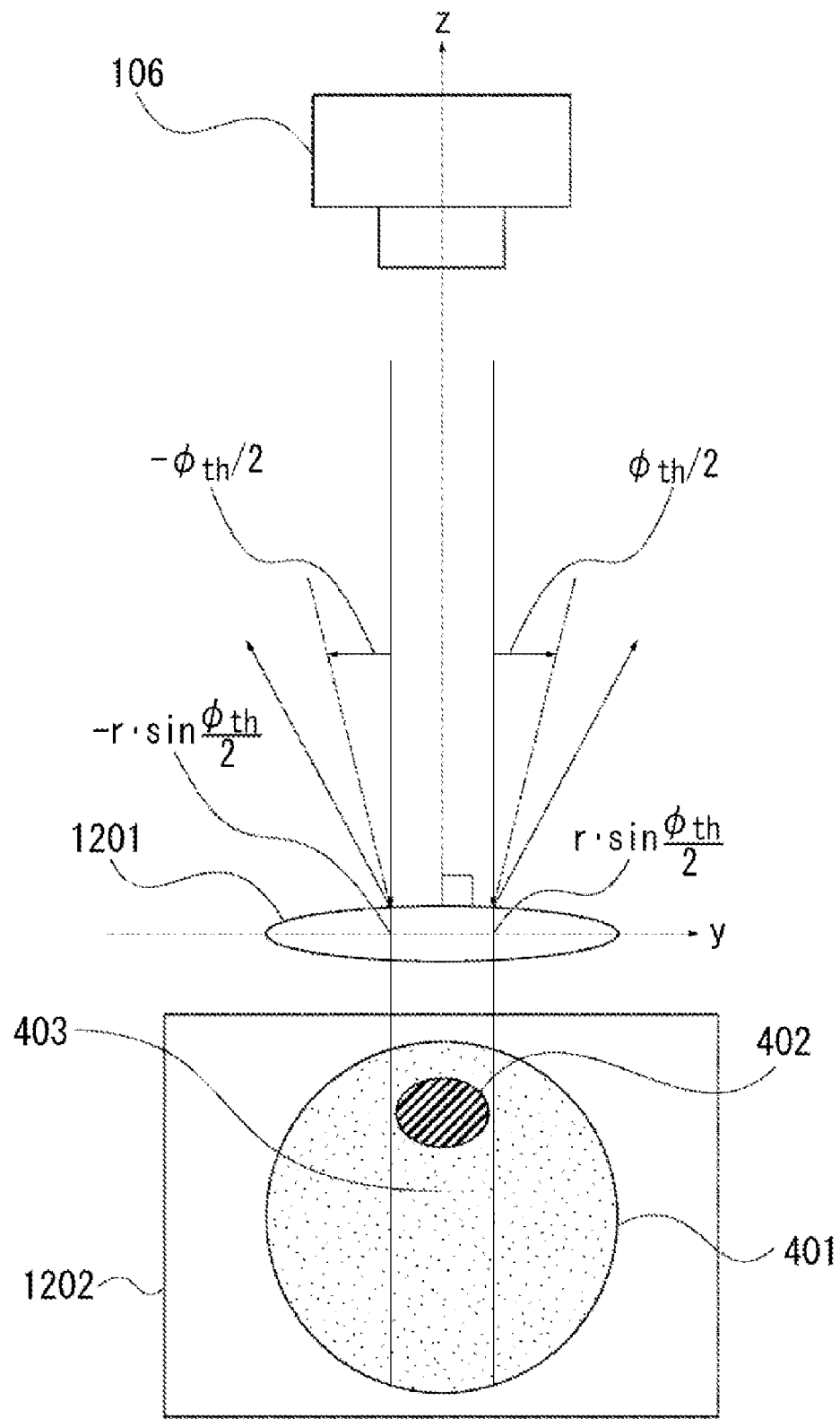
FIG. 14 illustrates a density nonuniformity inspection region and a defective site inspection region according to a second exemplary embodiment of the present invention.

FIG. 14 illustrates the density nonuniformity inspection region 402 and the defective site inspection region 403 in the present exemplary embodiment.

As described above, the divided regions in the captured image vary according to a position of the imaging unit 106, an inclination of the inspection target surface 1202, and an incident angle of an illumination light. In the present exemplary embodiment, the inspection target surface 102 is convex-shaped, and as illustrated in FIG. 14, the area of the density nonuniformity inspection region 402 is smaller than the area of the density nonuniformity inspection region 402 in the first exemplary embodiment. Therefore, the displacement of the inspection target 1201 needs to be greater than the displacement of the inspection target in the first exemplary embodiment to inspect the entire surface of the inspection target surface 1202.

In the present exemplary embodiment, a driving unit (not illustrated) is required to perform a process such as inclining the inspection target 1201 with respect to the imaging unit 106.

Figure 15B:
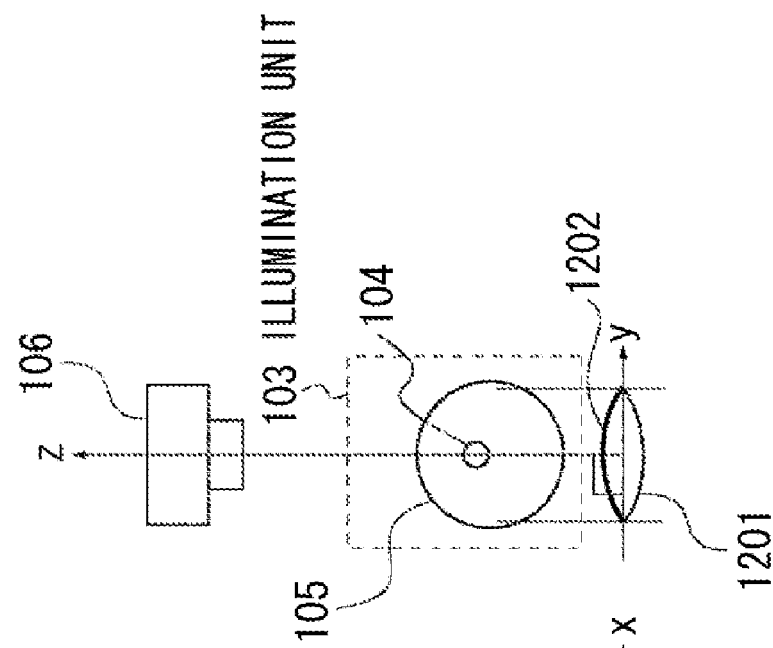
FIGS. 15A and 15B illustrate a state in which an inspection target is inclined with respect to an imaging unit according to a second exemplary embodiment of the present invention.
Figure 15A:
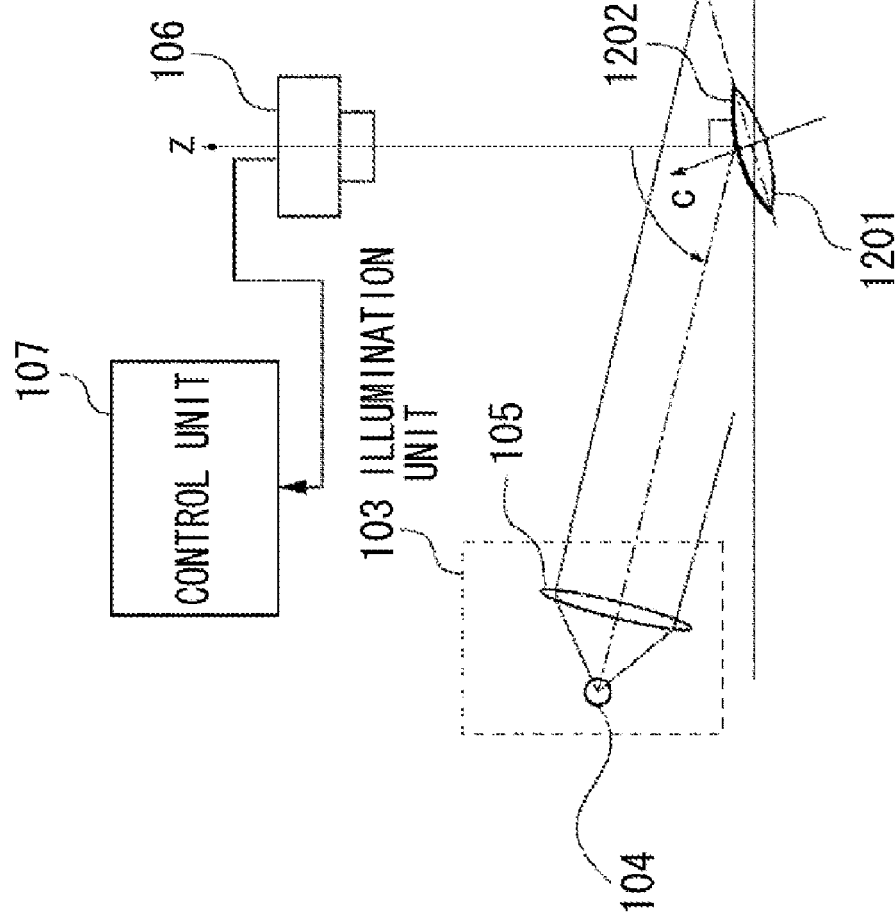

FIGS. 15A and 15B illustrate a state in which the inspection target 1201 is inclined with respect to the imaging unit 106. The density nonuniformity inspection region 402 in the captured image 401 changes according to the inclination angle η.

Figure 16:
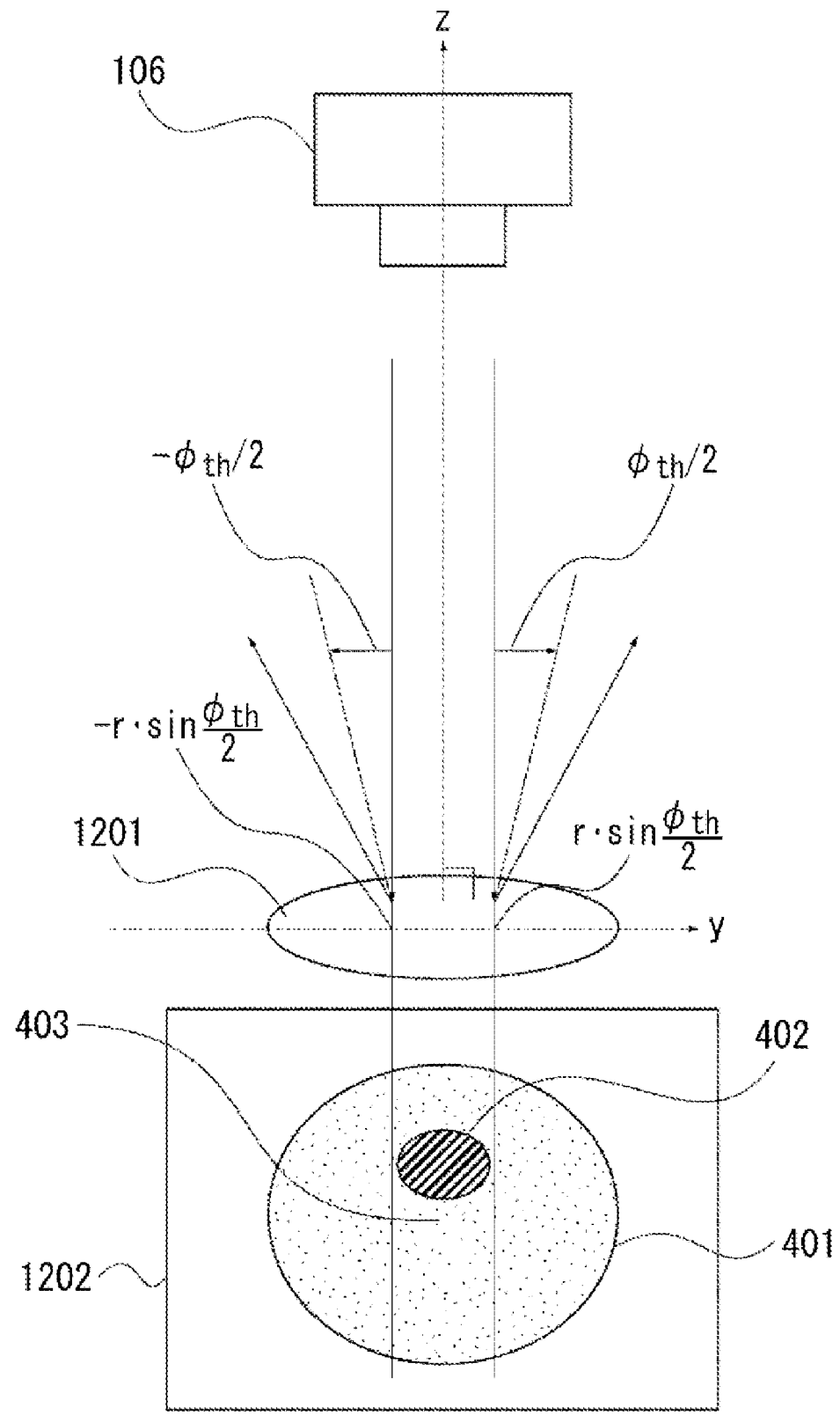
FIG. 16 illustrates a density nonuniformity inspection region and a defective site inspection region in a case where an inspection target is inclined with respect to an imaging unit according to a second exemplary embodiment of the present invention.

FIG. 16 illustrates the density nonuniformity inspection region 402 and the defective site inspection region 403 in a case where the inspection target 1201 is inclined with respect to the imaging unit 106. Referring to FIG. 16, by inclining the inspection target 1201, the density nonuniformity inspection region 402 is located at a different position from the position illustrated in FIG. 14. However, the density nonuniformity inspection region 402 is displaced only in the vertical direction in FIG. 16 if only the inspection target 1201 is inclined.

Therefore, in addition to inclining the inspection target 1201, a driving unit (not illustrated) rotates the inspection target 1201 around a c-axis illustrated in FIG. 15, so that a captured image is acquired at every predetermined angle. As a result, surface inspection can be performed on the entire surface of the inspection target surface 1202.

Third Exemplary Embodiment

In the first and second exemplary embodiments, the captured image 401 is divided into two types of regions, i.e., the density nonuniformity inspection region 402 and the defective site inspection region 403. In the present exemplary embodiment, the captured image 401 is divided into three or more types of regions.

Figure 17:
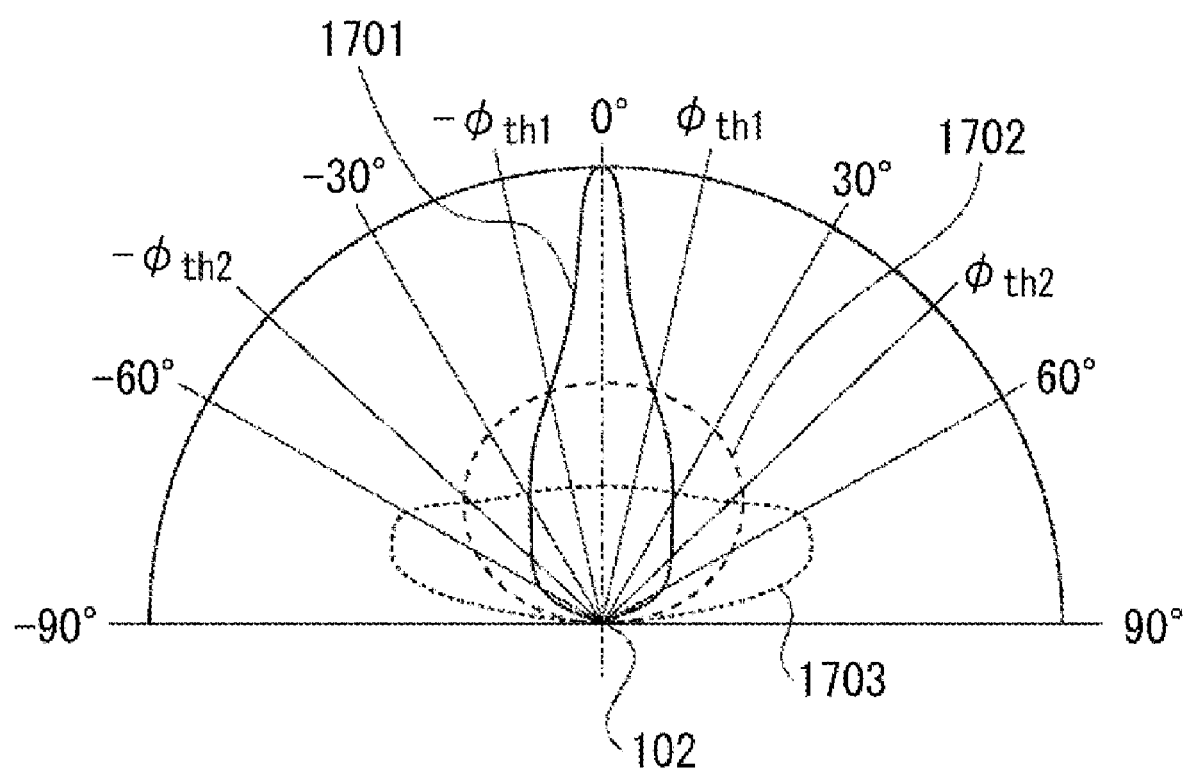
FIG. 17 illustrates three types of diffuse-reflected light curves.

FIG. 17 illustrates three types of diffuse-reflected light curves that are obtained using the gonio-photometer illustrated in FIG. 5.

Diffuse-reflected light curves 1701, 1702, and 1703 are curves that are each caused by different structures of the inspection target surface 102. Threshold values $\Phi_{th1}$ and $\Phi_{th2}$ that are used to divide the captured image 401 into appropriate inspection regions can be obtained from intersecting points of the diffuse-reflected light curves 1701, 1702, and 1703.

Figure 18:
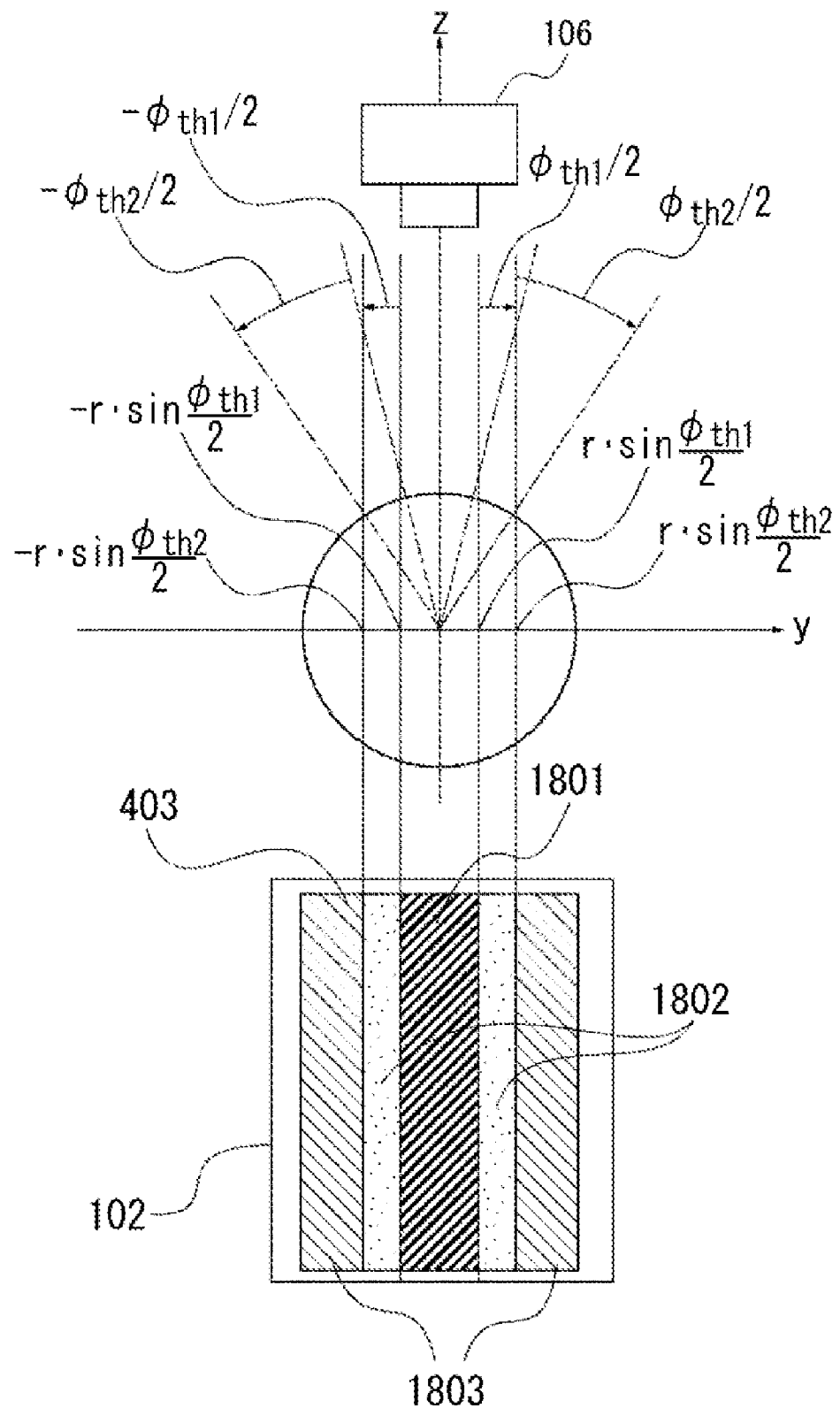
FIG. 18 illustrates division of a captured image based on threshold values $\Phi_{th1}$, $\Phi_{th2}$ according to a third exemplary embodiment of the present invention.

FIG. 18 illustrates a division of a captured image based on the threshold values $\Phi_{th1}$ and $\Phi_{th2}$. Regions based on the threshold values $\Phi_{th1}$ and $\Phi_{th2}$ are set according to an empirical rule, similar to the first exemplary embodiment.

A first inspection region 1801 is a region between $-r \cdot \sin \Phi_{th1}/2$ and $r \cdot \sin \Phi_{th1}/2$ with respect to a y-axis.

A second inspection region 1802 is a region between $-r \cdot \sin \Phi_{th1}/2$ and $-r \cdot \sin \Phi_{th2}/2$ and between $r \cdot \sin \Phi_{th1}/2$ and $r \cdot \sin \Phi_{th2}/2$, with respect to the y-axis.

A third inspection region 1803 is a region other than the first inspection region 1801 and the second inspection region 1802.

The ranges of the first inspection region 1801, the second inspection region 1802, and the third inspection region 1803 can be changed according to a position of the imaging unit 106, an incident angle of an illumination light, and an inclination of the inspection target surface 102.

Three or more types of surface inspection can thus be performed by changing the processes performed in steps 302 and 303 illustrated in FIG. 3 in the first exemplary embodiment, based on the above-described threshold values.

While the present invention has been described with reference to exemplary embodiments, it is to be understood that the invention is not limited to the disclosed exemplary embodiments. The scope of the following claims is to be accorded the broadest interpretation so as to encompass all modifications, equivalent structures, and functions.

This application claims priority from Japanese Patent Application No. 2007-182954 filed Jul. 12, 2007, which is hereby incorporated by reference herein in its entirety.

What is claimed is:

1. An inspection apparatus comprising:
    a captured image acquiring unit configured to acquire a captured image that is acquired by shooting an inspection target;
    an acquiring unit configured to acquire from the captured image a first image region and a second image region whose intensity distributions of reflected light with respect to an incident angle of illumination light emitted to the inspection target are different; and
    an image processing unit configured to perform image processing for different surface inspections on the first image region and the second image region respectively.

2. The inspection apparatus according to claim 1, wherein the image processing unit performs image processing on the first image region for performing the first surface inspection and performs image processing on the second image region for performing the second surface inspection.

3. The inspection apparatus according to claim 1, further comprising:
    a sensor unit configured to capture the inspection target; and
    an illumination unit configured to illuminate the inspection target,
    wherein the acquiring unit acquires the first image region and the second image region from the captured image based on relative positions of the illumination unit, the sensor unit, and a shape of the inspection target.

4. The inspection apparatus according to claim 1, further comprising a threshold acquiring unit configured to, when illumination light is irradiated in a direction perpendicular to the inspection target surface, acquire as a threshold value an angle at which a proportion of luminance of reflected light caused by a first surface shape of the inspection target and luminance of reflected light caused by a second surface shape of the inspection target changes,
    wherein the acquiring unit acquires the first image region and the second image region from the captured image based on the threshold value.

5. The inspection apparatus according to claim 4, wherein the first image region is a region in which a portion of reflected light caused by the first surface shape that is more than that caused by the second surface shape is included, and the second image region is a region in which a portion of reflected light caused by the second surface shape that is more than reflected light caused by the first surface shape is included.

6. The inspection apparatus according to claim 5, wherein the first surface shape is a density nonuniformity region of a surface of the inspection target, and wherein the second surface shape is a defect in a surface shape of the inspection target.

7. The inspection apparatus according to claim 1, wherein the inspection target includes a cylindrical portion, and
    the inspection apparatus further comprising a driving unit configured to rotate the inspection target around a central axis of the cylindrical portion,
    wherein the captured image acquiring unit acquires the captured image at each rotation of a predetermined angle of the inspection target caused by the driving unit.

8. The inspection apparatus according to claim 1, wherein the inspection target includes a spherical portion, and
    the inspection apparatus further comprising a driving unit configured to incline the inspection target,
    wherein the captured image acquiring unit acquires the captured image at each inclination of a predetermined angle of the inspection target caused by the driving unit.

9. An inspection apparatus comprising:
    a captured image acquiring unit configured to acquire a captured image that is acquired by shooting an inspection target;
    an acquiring unit configured to acquire a first image region and a second image region whose intensity distributions of reflected light with respect to an incident angle of illumination light emitted to the inspection target are different, based on the luminance distribution of the captured image; and
    an image processing unit configured to perform image processing for performing different surface inspections on the first image region and the second image region respectively.

10. A method comprising:
    acquiring a captured image that is acquired by shooting an inspection target;
    acquiring from the captured image a first image region and a second image region whose intensity distributions of reflected light with respect to an incident angle of illumination light emitted to the inspection target are different; and
    performing image processing for different surface inspections on the first image region and the second image region respectively.

11. A computer-readable storage medium storing a program of instructions which cause the computer to perform a method comprising:
    acquiring a captured image that is acquired by shooting an inspection target;
    acquiring from the captured image a first image region and a second image region whose intensity distributions of reflected light with respect to an incident angle of illumination light emitted to the inspection target are different; and
    performing image processing for different surface inspections on the first image region and the second image region respectively.

* * * * *